United States Patent
Bechtold et al.

(10) Patent No.: US 6,849,053 B2
(45) Date of Patent: *Feb. 1, 2005

(54) SHOCK WAVE SOURCE WITH A WAVE DAMPING COIL CARRIER

(75) Inventors: Mario Bechtold, Röttenbach (DE); Jens Fehre, Hausen (DE); Bernd Granz, Oberasbach (DE); Matthias Mahler, Erlangen (DE)

(73) Assignee: Siemens Aktiengesellschaft, Münich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/238,566

(22) Filed: Sep. 10, 2002

(65) Prior Publication Data

US 2003/0069527 A1 Apr. 10, 2003

(30) Foreign Application Priority Data

Sep. 10, 2001 (DE) .......................................... 101 44 421

(51) Int. Cl.⁷ .............................................. A61B 17/00
(52) U.S. Cl. ........................... 601/4; 310/327; 367/162; 367/176; 181/207; 181/208; 181/209
(58) Field of Search ..................... 601/2, 4; 181/207, 181/208, 209, 210; 600/439; 310/327; 604/22; 367/140, 162, 176; 381/71.2

(56) References Cited

U.S. PATENT DOCUMENTS

| 4,301,890 A | | 11/1981 | Zalas |
| 4,721,106 A | | 1/1988 | Kurtze et al. |
| 4,807,627 A | * | 2/1989 | Eisenmenger .................. 601/4 |
| 4,972,826 A | * | 11/1990 | Koehler et al. ................. 601/4 |
| 5,394,786 A | * | 3/1995 | Gettle et al. ................... 86/50 |
| 5,941,838 A | | 8/1999 | Eizenhöfer |
| 6,179,792 B1 | | 1/2001 | Krause |
| 6,302,857 B1 | * | 10/2001 | Landeck ........................ 601/4 |
| 2003/0060738 A1 | * | 3/2003 | Ein-gal ........................... 601/4 |

FOREIGN PATENT DOCUMENTS

| DE | OS 35 05 855 | 8/1986 |
| DE | 8618166.1 | 7/1988 |
| EP | 0 189 781 | 5/1989 |

OTHER PUBLICATIONS

Electromagnetic Acoustic Source for the Extracorporeal Generation of Shock Waves in Lithotripsy, Reichenberger et al. Siemens Forschungs–und Entwicklungbricht, vol. 15, No. 4 (1986) pp. 187–194.

"Elektromagnetische Erzeugung von Ebenen Druckstörssen in Flüssigkeiten," Eisenmenger, Acustica, vol. 1 (1962), pp. 185–186.

* cited by examiner

Primary Examiner—Eleni Mantis Mercader
(74) Attorney, Agent, or Firm—Schiff Hardin LLP

(57) ABSTRACT

A shock wave source has a coil carrier, a coil, having a metallic membrane separated from the coil in insulating fashion for generating shock waves. The coil carrier is formed of a material that damps the formation and/or the propagation of audible acoustic waves in the generation of shock waves.

16 Claims, 3 Drawing Sheets

SHOCK WAVE SOURCE WITH A WAVE DAMPING COIL CARRIER

BACKGROUND OF THE INVENTION

1. Field of the Invention

The present invention is directed to a shock wave source of the type having a coil carrier, a coil and a metallic membrane separated from the coil in insulating fashion for generating shock waves.

2. Description of the Prior Art

Electromagnetic shock wave sources of the type described above are utilized, for example, in medicine for the non-invasive disintegration of body calculi of a patient, for example for the disintegration of kidney stones. The generation of shock waves with such a shock wave source is accomplished by a brief-duration high-voltage pulse applied to the coil arranged on the coil carrier. As a result of the electromagnetic interaction of the coil with the metallic membrane separated from it in insulating fashion, the membrane is repelled from the coil in an enclosed volume of water located between the shock wave source and the patient. As a result, attenuated sine waves are emitted into the water as carrier medium between the shock wave source and the patient. Shock waves ultimately arise due to non-linear effects in the carrier medium, water. The attenuated sine oscillations have a basic frequency of about 150 through 200 kHz that is determined by the electrical properties of the shock wave source. The sine waves lie outside the human hearing range.

Nevertheless, audible waves arise when generating shock waves with an electromagnetic shock wave source—as described, moreover, in structure and function in, for example, H. Reichenberger, G. Naser, "Electromagnetic Acoustic Source for the Extracorporeal Generation of Shock Waves in Lithotripsy", Siemens Forschungs-und Entwicklungsberichte, 15, 1986, No. 4, pages 187 through 194. Simultaneously with the emission of the sine waves into the water path, waves propagate in the opposite direction in the coil carrier (usually formed of ceramic) that can convert initially axially propagating waves into radial or plate waves. The radial or plate waves cause the coil carrier to oscillate such that low-frequency waves arise in the human hearing range, i.e. below 20 kHz. Due to the highly symmetrical geometrical shape of the coil carrier (the coil carrier usually has a circular cross-section in planes at a right angle to its longitudinal axis) equiphase superimpositions of radial and plate waves also occur due to reflections at the edge of the coil carrier. As a result, audible waves arise that have a very unpleasant sound level for patients and medical personnel.

SUMMARY OF THE INVENTION

An object of the present invention to provide a shock wave source of the type initially described wherein the generation of audible acoustic waves is reduced in the generation of shock waves.

This object is inventively achieved in a shock wave source having a coil carrier, a coil and a metallic membrane separated from the coil in insulating fashion for generating shock waves, wherein the coil carrier is formed of a material that damps the formation and/or propagation of waves. Differing from a coil carrier formed of a ceramic material as disclosed, for example, in German OS 35 02 770 and German OS 35 05 855, a coil carrier fashioned of a material that damps the formation and/or the propagation of waves additionally reduces the generation of acoustic waves in the generation of shock waves, since it is not only the axial propagation of high-frequency waves having a basic frequency between approximately 100 and 200 kHz in the direction of the coil carrier that is damped, but also their conversion into low-frequency radial waves or plate waves. Thus the formation of radial waves or plate waves that cause the coil carrier to oscillate, as well as their propagation, are both noticeably reduced. Accordingly, the coil carrier is excited less to oscillate, and thus noticeably fewer acoustic waves are generated in the generation of shock waves.

In one version of the invention the material of the coil carrier that damps the formation and/or propagation of waves has a mechanical vibrational Q of less than 100, preferably less than 50. The value of Q is a criterion for the capability of a material to oscillate. In comparison thereto, the ceramic material conventionally employed for coil carriers has a Q of approximately 1000.

In further embodiments of the invention the material for the coil carrier contains rubber or plastic. The coil carrier can alternatively be entirely fashioned of rubber or plastic. The material preferably is provided with electrically non-conductive particles in order to obtain a heterogeneous material that usually damps the formation and/or the propagation of waves better than a homogeneous material. According to a further version of the invention, the particles are formed of a material that has a higher hardness than the material that damps the formation and/or the propagation of waves. A higher strength, and thus a higher dimensional stability of the coil carrier, are achieved in this way.

In another embodiment of the invention the material damping the formation and/or the propagation of waves is an expanded plastic. A suitable expanded plastic is, for example, PUR high-resistance foam as distributed by IVPU Industrieverband, Polyurethan-Hartschaum e.V., Stuttgart.

In a further version of the invention, the material that damps the formation and/or the propagation of waves has a honeycomb structure. The material is plastic or resin-bonded paper according to one version of the invention. The honeycomb structure can be composed of regular and/or irregular polygons. A suitable material of plastic or resin-bonded paper having a honeycomb structure is distributed, for example, by Euro-Composites, Zone Industrielle, Luxemburg. A coil carrier that is fashioned of such a material having a honeycomb structure also noticeably reduces the formation of low-frequency waves and noticeably damps the propagation of low-frequency and high-frequency waves. As a result the generation of acoustic waves is significantly reduced when generating shock waves.

In another embodiment of the invention the coil carrier has a longitudinal axis, and the coil carrier is fashioned such that a cross-sectional area of the coil carrier intersected at a right angle by its longitudinal axis has a non-circular contour. Inventively, this represents a rejection of a high degree of symmetry of the coil carrier. This said high degree of symmetry contributes to the disadvantage that radial or plate waves forming during the course of generating shock waves and superimposing equiphase due to reflection at the edge surfaces of the coil carrier, resulting in acoustic waves having a higher sound level being generated. By departing from this high degree of symmetry, the equiphase superimposition of, in particular, radial waves and plate waves is at least reduced, so that the generation of acoustic waves with a high sound level also is reduced.

In further versions of the invention the cross-sectional area of the coil carrier can have a contour with corners, an irregularly proceeding contour or a regularly proceeding, non-circular contour that can have corners and rounded portions. As a result equiphase superimpositioned radial waves and plate waves are prevented or at least significantly reduced, as already mentioned.

In another version of the invention the coil carrier has a generated surface with a first cover surface facing toward the coil and a second cover surface facing away from the coil. The second cover surface is fashioned non-flat. According to further versions of the invention, the second cover surface has depressions and/or elevations that can form a round or polygonal shapes and are preferably irregular. As a result of this design of the second cover surface, the conversion of axially propagating waves into radial or plate waves also can be noticeably reduced. Moreover, equiphase superimposition of radial or plate waves can be reduced, so that there is a reduction on the excitation of the coil carrier to oscillate and, accordingly, the generation of acoustic waves is noticeably reduced.

DESCRIPTION OF THE PREFERRED EMBODIMENTS

Figure 1:
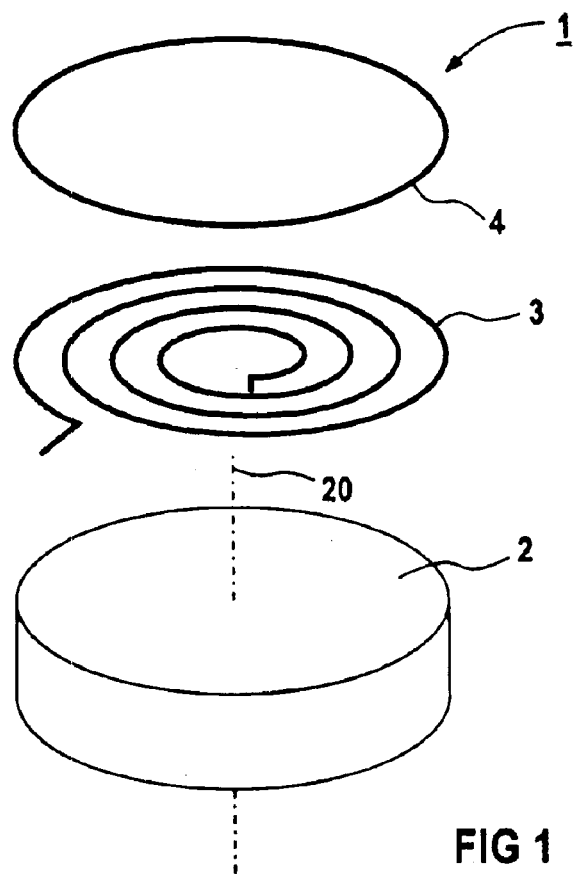
FIGS. 1 and 2 are schematic illustrations showing the structure of an electromagnetic shock wave source having a coil carrier.
Figure 2:
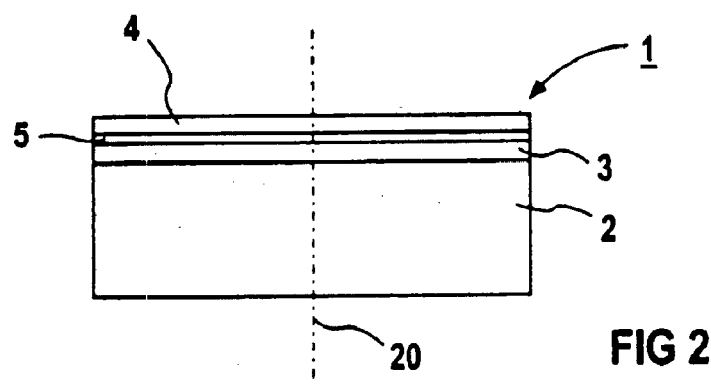

FIG. 1 shows a highly schematic illustration of the components of a known electromagnetic shock wave source 1. In the exemplary embodiment, the shock wave source 1 has a disk-shaped coil carrier 2, a flat coil 3 and a metallic membrane 4. For illustrating the structure of the shock wave source 1, the coil carrier 2, the flat coil 3 and the membrane 4 are shown separated in FIG. 1. In the operational state of the shock wave source 1 shown in FIG. 2, the flat coil 3 lies on the coil carrier 2 and is separated from the metallic membrane 4 in insulating fashion by an insulating foil 5 (not shown in FIG. 1). When generating shock waves, a brief-duration high-voltage pulse is applied to the flat coil 3 arranged on the coil carrier 2. Due to the electromagnetic interaction of the flat coil 3 with the membrane 4 separated therefrom in insulating fashion, this is repelled into an acoustic propagation medium (not explicitly shown in FIGS. 1 and 2), which is usually water. A shock wave is generated in this way; and can be introduced into the body of a patient via the propagation medium, water.

Since, as initially mentioned, acoustic waves with an unpleasant sound level also are generated when generating shock waves with such an electromagnetic shock wave source, in accordance with the invention the coil carrier is formed of a material that damps the formation of low-frequency waves and/or the propagation of high-frequency and low-frequency waves, so that the coil carrier is not excited to oscillate or is at least excited to oscillate only in a significantly diminished way, and thus no or at least noticeably fewer acoustic waves arise when generating shock waves. The material should have a Q of below 100, preferably below 50.

Figure 3:
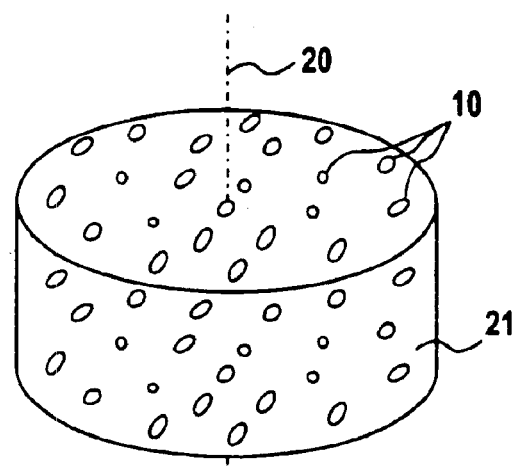
FIGS. 3 through 8 show inventive embodiments of a coil carrier for use in the shock wave source from FIGS. 1 and 2.
Figure 4:
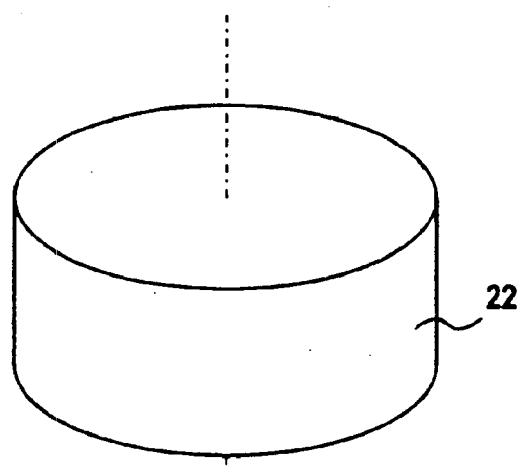
Figure 5:
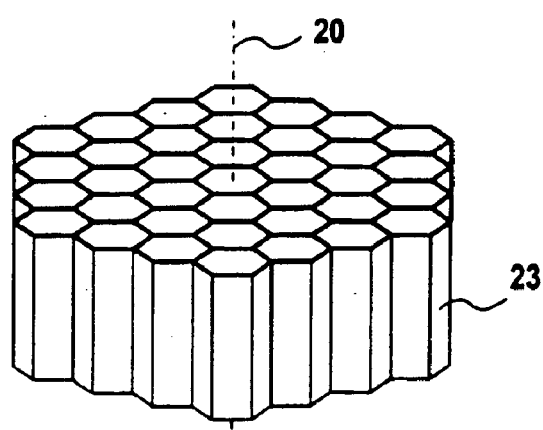

FIGS. 3 through 5 show coil carriers 21 through 23 that are fashioned of materials that damp the formation and/or propagation of waves and have a vibrational Q of below 50. The coil carrier 21 shown in FIG. 3 is formed of rubber or plastic and is laced with hard, electrically non-conductive particles 10. In the exemplary embodiment, the particles are of tungsten oxide or ceramic, which exhibit a higher hardness than rubber or plastic. The particles are provided in order to increase the strength of the coil carrier 21 and keep it dimensionally stable, as well as to form a heterogeneous material that usually damps the formation and propagation of waves even better than rubber or plastic per se.

FIG. 4 shows a coil carrier 22 that is fashioned of an expanded plastic. In the exemplary embodiment, the expanded plastic is a PUR high-resistance foam that is commonly utilized as a heat-damping material in and of itself. PUR high-resistance foam, however, also is suitable as material for a coil carrier since the formation and propagation of waves is damped in the coil carrier 22 when generating shock waves, so that noticeably fewer acoustic waves are generated when generating shock waves compared to a coil carrier that is formed of ceramic.

FIG. 5 shows a third inventive embodiment of a coil carrier composed of a material having a honeycomb structure. The material forming the honeycomb structure can be plastic, resin-bonded paper or some other material. For example, Euro-Composites, Luxemburg, distributes such a material having a honeycomb structure. The formation and propagation of waves can be damped with a coil carrier 23 fashioned of such a material, so that audible acoustic waves are generated to only a significantly reduced extent when generating shock waves with a shock wave source employing the coil carrier 23. The honeycomb structure can, moreover, be formed of regular polygons, i.e. triangles, quadrangles or—as in the case of the exemplary embodiment—hexagons and/or irregular polygons, which are understood to be polygons having an irregular edge course.

Figure 6:
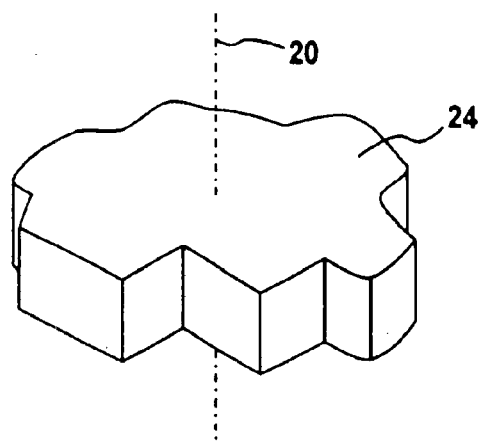
Figure 7:
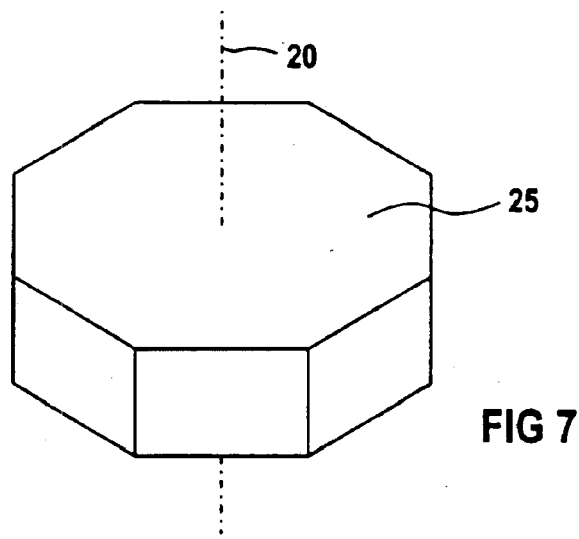
Figure 8:
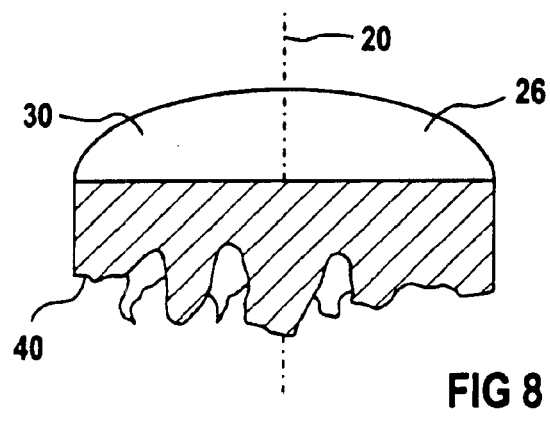

FIGS. 6 through 8 show further inventive embodiments of coil carriers 24 through 26 that can be formed of one of the described materials. The coil carriers 24 and 25 are characterized in that their design represents a departure from a high symmetry of a coil carrier. The coil carrier 2, as can be seen from FIG. 1, has a longitudinal axis 20. The coil carrier 2 comprises a high symmetry with respect to the longitudinal axis 20. An arbitrary cross-sectional area of the coil carrier 2 penetrated by the longitudinal axis at a right angle has a round contour, i.e. a contour of high symmetry. No modification of its outside contour (in a plan view onto the coil carrier) occurs when the cross-sectional area or the coil carrier is rotated around the longitudinal axis 20. This favors the equiphase superimposition of radial or plate waves that form during the generation of shock waves, and thus promotes a generation of low-frequency acoustic waves with high sound level.

In accordance with the invention, for the additional damping of waves, the coil carrier is fashioned such that a cross-sectional area of the coil carrier intersected by the longitudinal axis 20 at a right angle has a non-circular contour, so that the final contour generally does not coincide with the initial contour as a result of an arbitrary rotation of the cross-sectional area or the coil carrier around the longitudinal axis 20. Such contours are recognizable given a plan view onto the cross-sectional area or the coil carrier.

The coil carrier 24 shown in FIG. 6 is fashioned such that an arbitrary cross-sectional area that is intersected by the longitudinal axis 20 at a right angle has a non-circular contour, a contour with corners in the present case. Thus when radial or plate waves form, these are not reflected at the edges of the coil carrier 24, so that equiphase superimpositions of these waves is precluded. Such equiphase superimposition, when permitted to occur, results in an amplification of the waves and thus an intensified sound generation. The coil carrier 24 is fashioned such that the final contour corresponds to the initial contour only given a rotation by 360° around the longitudinal axis 20.

FIG. 7 shows a coil carrier 25 with a cross-sectional area penetrated by the longitudinal axis 20 at a right angle has a regularly fashioned, octagonal contour. Even though the contour is regular, the superimposition of plate or radial waves can be reduced by means of a departure from the round contour. However, the irregularly proceeding contour as shown in FIG. 6 is even more effective for avoiding such superimpositions than the fashioning of a coil carrier shown in FIG. 7.

The contour of a cross-sectional area intersected by the longitudinal axis 20 at a right angle need not, moreover, have only corners but can have rounded portions.

In another inventive embodiment of the coil carrier, the cover surface of the disk-shaped coil carrier facing away from the flat coil 3 is fashioned non-flat. FIG. 8 shows a section through an inventive coil carrier 26 in the direction of the longitudinal axis 20. As can be seen from FIG. 8, the cover surface 30 that faces toward the flat coil 3 and on which the flat coil 3 is arranged is flat. In contrast thereto, the second cover surface 40 of the coil carrier 26 facing away from the flat coil 3 is non-flat, provided with noticeable depressions and elevations in the present case. The depressions and/or elevations preferably are irregular. The depressions and/or elevations preferably extend over the entire cover surface. As a result, when generating shock waves, the waves propagating axially in the direction of the longitudinal axis 20 in the coil carrier 26 convert into plate or radial waves to a reduced extent, or not at all. Also achieved is that no or only a few equiphase superimpositions of axially propagating waves occur that could cause the coil carrier to oscillate. The generation of low-frequency acoustic waves in the generation of shock waves thus is significantly reduced in this way.

The inventive embodiments of a coil carrier for an electromagnetic shock wave source were presented and explained above independently of one another on the basis of FIGS. 3 through 8. The various embodiments of the coil carrier, however, can be combined with one another in arbitrary ways. For example, the coil carrier can be composed of PUR high-resistance foam, have a polygonal, irregular outside contour in plan view and the second cover surface thereof facing away from the flat coil can be provided with depressions and elevations. Other combinations of the embodiments of the inventive coil carrier explained individually in FIGS. 3 through 8 also can be unproblematically formed.

The coil carrier, moreover, need not necessarily be disk-shaped, nor need the coil be a flat coil.

Although modifications and changes may be suggested by those skilled in the art, it is the intention of the inventors to embody within the patent warranted hereon all changes and modifications as reasonably and properly come within the scope of their contribution to the art.

We claim as our invention:

1. A shock wave source comprising:
   a coil carrier;
   a coil disposed on said coil carrier;
   a membrane overlying said coil on said coil carrier and separated from said coil in electrically insulating fashion, said coil being disposed between said coil carrier and said membrane and interacting with said membrane, upon being charged with a current, to generate shock waves; and
   said coil carrier comprising a material which damps at least one of formation and propagation of waves in said coil carrier generated by said shock waves.

2. A shock wave source as claimed in claim 1 wherein said coil carrier comprises a material having a mechanical vibrational Q of below 100.

3. A shock wave source as claimed in claim 1 wherein said material is selected from the group consisting of rubber and plastic.

4. A shock wave source as claimed in claim 1 wherein said material is laced with particles.

5. A shock wave source as claimed in claim 4 wherein said particles have a hardness that is higher than a hardness of said material.

6. A shock wave source as claimed in claim 1 wherein said material is expanded plastic.

7. A shock wave source as claimed in claim 1 wherein said material has a honeycomb structure.

8. A shock wave source as claimed in claim 7 wherein said honeycomb structure is comprised of polygons selected from the group consisting of regular polygons and irregular polygons.

9. A shock wave source as claimed in claim 7 wherein said material comprising said honeycomb structure is selected from the group consisting of plastic and resin-bonded paper.

10. A shock wave source as claimed in claim 1 wherein said coil carrier has a longitudinal axis, and a cross-sectional area intersected by said longitudinal axis at a right angle having a non-circular contour.

11. A shock wave source as claimed in claim 10 wherein said cross-sectional area comprises a contour having corners.

12. A shock wave source as claimed in claim 10 wherein said cross-sectional area comprises an irregular contour.

13. A shock wave source as claimed in claim 10 wherein said cross-sectional area comprises a regular, non-circular contour.

14. A shock wave source as claimed in claim 1 wherein said coil carrier has a generated surface with a first cover surface facing toward said coil and a second cover surface facing away from said coil, said second cover surface being non-flat.

15. A shock wave source as claimed in claim 14 wherein said second cover surface has structures therein selected from the group consisting of depressions and elevations.

16. A shock wave source as claimed in claim 15 wherein said structures of said second cover surface are irregular.

* * * * *